(12) United States Patent
Okada et al.

(10) Patent No.: US 10,131,593 B2
(45) Date of Patent: Nov. 20, 2018

(54) SYSTEMS AND METHODS FOR PRODUCING HYDROGEN FROM A HYDROCARBON AND USING THE PRODUCED HYDROGEN IN A HYDROGENATION REACTION

(71) Applicant: CHIYODA CORPORATION, Kanagawa (JP)

(72) Inventors: Yoshimi Okada, Kanagawa (JP); Tomohiko Shirasaki, Kanagawa (JP); Osamu Ikeda, Kanagawa (JP); Kenichi Imagawa, Kanagawa (JP); Hironori Kawai, Kanagawa (JP); Masato Shiraga, Kanagawa (JP); Tatsuo Ishiyama, Kanagawa (JP)

(73) Assignee: CHIYODA CORPORATION, Kanagawa (JP)

( * ) Notice: Subject to any disclaimer, the term of this patent is extended or adjusted under 35 U.S.C. 154(b) by 151 days.

(21) Appl. No.: 14/910,161

(22) PCT Filed: Aug. 5, 2014

(86) PCT No.: PCT/JP2014/004094
§ 371 (c)(1),
(2) Date: Feb. 4, 2016

(87) PCT Pub. No.: WO2015/019608
PCT Pub. Date: Feb. 12, 2015

(65) Prior Publication Data
US 2016/0176784 A1 Jun. 23, 2016

(30) Foreign Application Priority Data

Aug. 6, 2013 (JP) .................................. 2013-163460
Aug. 6, 2013 (JP) .................................. 2013-163462

(51) Int. Cl.
*C07C 5/10* (2006.01)
*B01D 53/18* (2006.01)
(Continued)

(52) U.S. Cl.
CPC ............ *C07C 5/10* (2013.01); *B01D 53/1418* (2013.01); *B01D 53/1425* (2013.01);
(Continued)

(58) Field of Classification Search
CPC .... C01B 2203/0415; C01B 2203/0475; C01B 2203/043; C01B 3/52; C10K 1/005;
(Continued)

(56) References Cited

U.S. PATENT DOCUMENTS 3,694,344 A * 9/1972 Munro ...................... C01B 3/38
208/102
4,052,176 A * 10/1977 Child ................. B01D 53/1406
252/373

(Continued)

FOREIGN PATENT DOCUMENTS

JP     H05301023 A    11/1993
JP     2003040601 A    2/2003
(Continued)

OTHER PUBLICATIONS

International Search Report for International Application No. PCT/JP/004094, dated Sep. 9, 2014, 11 pages.
(Continued)

*Primary Examiner* — Imran Akram
(74) *Attorney, Agent, or Firm* — Armstrong Teasdale LLP (57) ABSTRACT

To reduce the emission of carbon dioxide and improve the energy efficiency in a hydrogen supply system. The hydrogen supply system (1) comprises: a reformer (5) for performing steam reforming of a hydrocarbon; a shift reaction unit (6) for producing a gas containing hydrogen and carbon
(Continued)

dioxide by causing a water gas shift reaction of a gas obtained from the reformer; a first absorber (36) for absorbing the carbon dioxide contained in the gas obtained from the shift reaction unit in an absorption liquid; a hydrogenation reaction unit (8) for producing a hydrogenated aromatic compound by causing a hydrogenation reaction of an aromatic compound with a gas that has passed through the first absorber; and a regenerator (37) for separating the carbon dioxide from the absorption liquid by re-circulating the absorption liquid from the first absorber and heating the absorption liquid with heat generated from the hydrogenation reaction.

8 Claims, 4 Drawing Sheets

(51) Int. Cl.

| | | |
|---|---|---|
| E21B 43/40 | (2006.01) | |
| C01B 3/38 | (2006.01) | |
| C01B 3/52 | (2006.01) | |
| B01D 53/14 | (2006.01) | |
| B01D 53/75 | (2006.01) | |
| B01J 19/24 | (2006.01) | |
| E21B 43/16 | (2006.01) | |
| B01D 53/047 | (2006.01) | |
| B01D 53/26 | (2006.01) | |

(52) U.S. Cl.
CPC ......... *B01D 53/1475* (2013.01); *B01D 53/18* (2013.01); *B01D 53/75* (2013.01); *B01J 19/245* (2013.01); *C01B 3/38* (2013.01); *C01B 3/52* (2013.01); *E21B 43/164* (2013.01); *E21B 43/40* (2013.01); *B01D 53/047* (2013.01); *B01D 53/265* (2013.01); *B01D 2252/20478* (2013.01); *B01D 2253/1124* (2013.01); *B01D 2256/16* (2013.01); *B01D 2257/304* (2013.01); *B01D 2257/502* (2013.01); *B01D 2257/7025* (2013.01); *B01J 2219/00051* (2013.01); *B01J 2219/24* (2013.01); *C01B 2203/0233* (2013.01); *C01B 2203/0283* (2013.01); *C01B 2203/043* (2013.01); *C01B 2203/0405* (2013.01); *C01B 2203/0415* (2013.01); *C01B 2203/0475* (2013.01); *C01B 2203/1058* (2013.01); *C01B 2203/1076* (2013.01); *C01B 2203/1235* (2013.01); *Y02C 10/06* (2013.01); *Y02C 20/20* (2013.01); *Y02P 20/152* (2015.11); *Y02P 20/156* (2015.11)

(58) Field of Classification Search
CPC ...... E21B 43/164; Y02C 10/06; Y02P 20/152; B01D 53/1475; B01D 53/18
See application file for complete search history.

(56) References Cited

U.S. PATENT DOCUMENTS

| | | | |
|---|---|---|---|
| 2009/0029446 A1* | 1/2009 | O'Rear | B01D 53/1475 |
| | | | 435/262.5 |
| 2010/0158776 A1* | 6/2010 | Drnevich | C01B 3/384 |
| | | | 423/220 |
| 2011/0015282 A1 | 1/2011 | Yagi et al. | |
| 2011/0296986 A1* | 12/2011 | Buhrman | B01D 45/16 |
| | | | 95/34 |
| 2012/0010304 A1 | 1/2012 | Tasaka | |
| 2012/0014853 A1 | 1/2012 | Feugnet et al. | |
| 2012/0316252 A1* | 12/2012 | Hodoshima | C01B 3/384 |
| | | | 518/728 |
| 2012/0317833 A1* | 12/2012 | Hodoshima | C01B 3/38 |
| | | | 34/517 |
| 2014/0357737 A1* | 12/2014 | Abbott | C10K 1/005 |
| | | | 518/704 |

FOREIGN PATENT DOCUMENTS

| | | |
|---|---|---|
| JP | 2005200254 A | 7/2005 |
| JP | 2007031255 A | 2/2007 |
| JP | 2007153726 A | 6/2007 |
| JP | 2008290927 A | 12/2008 |
| JP | 2009029676 A | 2/2009 |
| JP | 2009221057 A | 10/2009 |
| JP | 2012519649 A | 8/2012 |
| JP | 2012176879 A | 9/2012 |
| JP | 2013049601 A | 3/2013 |
| JP | 2013087021 A | 5/2013 |
| WO | 0104046 A1 | 1/2001 |
| WO | 2004026441 A1 | 4/2004 |

OTHER PUBLICATIONS

Okada, Y. et al., Development of Large-Scale Hydrogen Storage and Transportation System Aiming at Realizing Low-carbon Society, Proceedings of the Society of Chemical Engineers, Japan: 75th Annual Meeting, Mar. 19, 2010, 1 page, The Society of Chemical Engineers, Japan.

Okada, Y. et al., Vision of Global Hydrogen Supply Chain and Development of Hydrogen Storage and Transportation System by the Organic Chemical Hydride Method, Hydrogen Energy Systems, Dec. 2008, pp. 8-12, vol. 33, No. 4, Hydrogen Energy Systems Society of Japan.

Third Party Observation, PCT/JP2014/004094, dated Sep. 2, 2015, 8 pages.

Dan G. Chapel et al., Recovery of CO2 from Flue Gases: Commercial Trends, Canadian Society of Chemical Engineers annual meeting, Oct. 4-6, 1999, Saskatchewan, Canada, pp. 1-16.

European Search Report, EP Application No. 14834642.2, dated Nov. 29, 2017, 9 pps.

* cited by examiner

SYSTEMS AND METHODS FOR PRODUCING HYDROGEN FROM A HYDROCARBON AND USING THE PRODUCED HYDROGEN IN A HYDROGENATION REACTION

TECHNICAL FIELD

The present invention relates to a hydrogen supply system and a hydrogen supply method for producing hydrogen from a hydrocarbon and supplying the produced hydrogen.

BACKGROUND ART

With the view of reducing the emission of carbon dioxide gas which is known as a major cause of global warming, there is a growing movement to use hydrogen gas that contains no carbon instead of hydrocarbons such as petroleum. In the field of transportation, extensive research efforts have been directed to hydrogen vehicles that directly burn hydrogen gas and fuel cell vehicles using fuel cells. Fixed fuel cells for cogeneration purposes are also being actively developed.

Hydrogen gas can be produced by the reforming of hydrocarbons and the electrolysis of water. Steam reforming is one of possible reforming processes, and produces hydrogen and carbon monoxide by causing a reaction between steam and hydrocarbons such as natural gas and naphtha at a high temperature in the presence of a catalyst. See Patent Document 1, for instance. The carbon monoxide obtained by the steam reforming is caused to react with water in a water gas shift reaction, thereby producing hydrogen and carbon dioxide gases.

When hydrogen gas is produced by reforming hydrocarbons, carbon dioxide is inevitably produced as a byproduct. Therefore, in order to prevent the carbon dioxide from being released to the atmosphere and avoid contributing to global warming, the carbon dioxide gas is required to be separated from the hydrogen gas, and stored in an appropriate manner. As a method for removing carbon dioxide gas from any gas, it is known to cause the gas containing the carbon dioxide gas to contact an absorption liquid such as alkanolamine water solution that absorbs carbon dioxide, and to be absorbed therein. See Patent Document 2, for instance. The absorption liquid that has absorbed carbon dioxide releases the carbon dioxide gas by means of a regeneration process consisting of a heating process. The regenerated absorption liquid can be recycled to be used once again. By using this method, carbon dioxide gas can be separated from the hydrogen gas. The separated carbon dioxide can be prevented from being released to the atmosphere, for instance, by being stored underground or under the sea. By thus recovering and storing (CCS) the carbon dioxide gas, the hydrogen gas can be utilized as clean energy that does not produce carbon dioxide even during the production process.

PRIOR ART DOCUMENT(S)

Patent Document(s)

[Patent Document 1] JP2013-49601A
[Patent Document 2] JPH05-301023A

SUMMARY OF THE INVENTION

Task to be Accomplished by the Invention

However, when the heat balance of the hydrogen production process is considered, it can be appreciated that external heat is required for the regeneration process because the heat required for the regeneration (heating) process of the absorption liquid that has absorbed carbon dioxide is not entirely available from within. Therefore, a significant amount of energy has to be introduced from without during the production of hydrogen, and when energy derived from fossil fuel is used, the emission of carbon dioxide gas increases in proportion to the increase in the amount of the consumption of the energy. Also, because the sites for storing carbon dioxide gas in underground are limited, when hydrogen is produced in an area adjacent to the users of the produced hydrogen, storing of the hydrogen in underground may not be feasible. In such a case, a challenge arises with the technology, the cost and the energy that are required to transport a large amount of carbon dioxide gas in an efficient manner to a site where the storage of carbon dioxide in underground is possible.

In view of such problems of the prior art, a primary object of the present invention is to reduce the emission of carbon dioxide gas and improve the energy efficiency in a hydrogen supply system and a hydrogen supply method.

Means to Accomplish the Task

To achieve such an object, the present invention provides a hydrogen supply system (1), comprising: a reformer (5) for performing steam reforming of a hydrocarbon; a shift reaction unit (6) for producing a gas containing hydrogen and carbon dioxide by causing a water gas shift reaction of a gas obtained from the reformer; a first absorber (36) for absorbing the carbon dioxide contained in the gas obtained from the shift reaction unit in an absorption liquid; a hydrogenation reaction unit (9) for producing a hydrogenated aromatic compound by causing a hydrogenation reaction of an aromatic compound with a gas that has passed through the first absorber; and a regenerator (37) for separating the carbon dioxide from the absorption liquid by re-circulating the absorption liquid from the first absorber and heating the absorption liquid with heat generated from the hydrogenation reaction.

In this arrangement, because the hydrogenation reaction of the aromatic compound is performed by using the produced hydrogen, and the heat produced from the hydrogenation reaction is used for the regeneration process of the absorption liquid that has absorbed the carbon dioxide, the heat balance of the hydrogen supply system can be improved. Therefore, the necessary supply of external energy can be minimized, and the emission of carbon dioxide (carbon dioxide gas) can be reduced.

Furthermore, the produced hydrogen is converted into the hydrogenated aromatic compound (organic hydride) which is in liquid form at normal temperature so that the transportation of the produced hydrogen can be facilitated. Because the hydrogenated aromatic compound readily releases the hydrogen by a dehydrogenation reaction, the hydrogen can be supplied in response to a demand for the hydrogen. Because the transportation of the hydrogen is simplified by converting the hydrogen into the hydrogenated aromatic compound, it is possible to form a system in which the facility (a plant or a device) for producing hydrogen from a hydrocarbon is located in an area remote from the user of the hydrogen, and the hydrogen is produced from the hydrogenated aromatic compound in an area of the user of the hydrogen or an area close to the user of the hydrogen. In other words, the facility for producing hydrogen can be located in an area suited for the storage of hydrogen gas in underground or an area where the hydrocarbon is mined or extracted, without regard to the location of the user of the hydrogen. Thereby, the need for transporting the carbon dioxide that is produced during the production process of the hydrogen can be eliminated, and the cost and energy associated with the transportation can be minimized.

In this invention, it may be arranged such that the hydrogen supply system further comprises a heating furnace (28) for supplying heat to the reformer; and a second absorber (38) for absorbing the carbon dioxide generated from the heating furnace in an absorption liquid; wherein the second absorber re-circulates the absorption liquid to the regenerator, and the absorption liquid that has absorbed the carbon dioxide in the second absorber is heated in the regenerator to separate the carbon dioxide therefrom.

According to this arrangement, the carbon dioxide that has been released by the heating in the reformer is recovered so that the emission of carbon dioxide from the hydrogen supply system can be minimized.

In this invention, it may be arranged such that the hydrogen supply system further comprises a hydrogen separation unit (8) for separating the hydrogen from the gas that has passed through the first absorber, and supplying the separated hydrogen to the hydrogenation reaction unit, combustion heat of the gas remaining after the hydrogen is separated in the hydrogen separation unit being supplied to the heating furnace.

According to this arrangement, because the concentration of the hydrogen in the gas that has passed through the hydrogen separation unit is increased, and the highly concentrated hydrogen is supplied to the hydrogenation reaction unit, the efficiency of the hydrogenation reaction in the hydrogenation reaction unit can be improved.

In this invention, it may be arranged such that the heat generated by the hydrogenation reaction is supplied to the regenerator as steam at a temperature of 100 to 200° C. and a pressure of 0.10 to 1.62 MPaA.

According to this arrangement, the heat from the hydrogen separation unit can be supplied to the regenerator by using readily available methods.

In this invention, it may be arranged such that the system further comprises a pressure injection unit (121, 141) for pressure injecting the carbon dioxide that is separated from the absorption liquid by the regenerator into a pressure injection well in order to increase a fluidity of the fossil fuel buried underground when extracting the fossil fuel buried underground, the reformer reforming at least a part of product gas produced as the fossil fuel or associated gas thereof that is extracted from a production well for extracting the fossil fuel.

According to this arrangement, when extracting fossil fuel by injecting gas or the like under pressure into the ground, the carbon content of the hydrocarbons contained in the product gas (including the associated gas) can be effectively utilized as the gas (carbon dioxide) that is to be injected into the ground.

In this invention, it may be arranged such that the system further comprises a first separation unit (7) for separating the hydrogen and the carbon dioxide in the gas obtained from the shift reaction unit from each other by using inorganic membrane.

According to this arrangement, by using an inorganic membrane made of inorganic material superior in corrosion resistance and separation selectivity, the hydrogen and the carbon dioxide can be separated from each other in an efficient manner without compromising separation selectivity so that the carbon atoms that form a part of the hydrocarbons contained in the produced gas can be effectively utilized as the carbon dioxide to be pressure injected, and the hydrogen atoms can be effectively utilized as hydrogen energy. Typically, organic membranes (made of materials such as cellulose acetate and polyimide) are used in carbon dioxide separation units, but because organic membranes may rapidly degenerate if the gas contains sulfuric components (such as hydrogen sulfate), the use of inorganic membrane can avoid such rapid degeneration.

In this invention, it may be arranged such that the production well is provided in an oil field (102) for extracting petroleum, and the petroleum is extracted as the fossil fuel.

According to this arrangement, when extracting petroleum by pressure injecting carbon dioxide, the hydrogen atoms that form a part of the hydrocarbons contained in the associated gas extracted with the petroleum can be effectively utilized.

In this invention, it may be arranged such that the production well is provided in a shale formation (140) for extracting natural gas, and the natural gas is extracted as the fossil fuel.

According to this arrangement, when extracting natural gas (shale gas) by pressure injecting carbon dioxide, the hydrogen atoms that form a part of the hydrocarbons contained in the natural gas can be effectively utilized. Also, by injecting carbon dioxide gas into both an oil field and a shale formation to extract fossil fuel buried in the oil field and the shale formation with the common single hydrogen supply system (fossil fuel extraction system), the amounts of injected carbon dioxide can be adjusted more easily, and the fossil fuel can be extracted in a more stable manner.

In this invention, it may be arranged such that the system further comprises a desulfurization unit (22) for removing a sulfur content from the product gas before the product gas is reformed by the reformer.

According to this arrangement, by removing sulfur contents from the produced gas, the poisoning of the catalyst in the reformer and the corrosion of the organic membrane by the sulfur contents can be avoided so that the hydrogen atoms that form a part of the hydrocarbons in the produced gas can be extracted in a stable manner.

In this invention, it may be arranged such that the product gas includes the natural gas extracted from the shale formation and the pressure injected carbon dioxide, and the system further comprises a second separation unit (145) for separating the natural gas and the carbon dioxide of the product gas from each other, the reformer reforming at least part of the natural gas separated by the second separation unit, and the pressure injection unit pressure injecting the carbon dioxide separated by the second separation unit into the pressure injection well in order to increase a fluidity of the fossil fuel buried underground.

According to this arrangement, the natural gas extracted from the shale formation includes the carbon dioxide that was injected into the injection well, and by separating the carbon dioxide gas therefrom for repeated use, even when the amount the carbon dioxide naturally existing in the shale formation is small, the extraction of natural gas can be continued without requiring a special facility for producing carbon dioxide.

Another aspect of the present invention provides hydrogen supply method, comprising: a hydrogen generation step for generating a gas containing hydrogen and carbon dioxide by a steam reforming of a hydrocarbon and a water gas shift reaction of a gas obtained by the steam reforming; an absorption step for absorbing the carbon dioxide contained in the gas obtained by the hydrogen generation step in an absorption liquid; a hydrogenation step for producing a hydrogenated aromatic compound by causing a hydrogenation reaction of an aromatic compound with the gas that has been processed by the absorption step; and a regeneration step for separating the carbon dioxide from the absorption liquid by heating the absorption liquid that has absorbed the carbon dioxide by using heat that has been generated by the hydrogenation reaction.

According to this arrangement, because the hydrogenation reaction of the aromatic compound is performed by using the produced hydrogen, and the heat produced from the hydrogenation reaction is used for the regeneration process of the absorption liquid that has absorbed the carbon dioxide, the heat balance of the hydrogen supply system can be improved. Furthermore, because the produced hydrogen is converted into the hydrogenated aromatic compound, the transportation and handling of the hydrogen can be facilitated.

In this invention, it may be arranged such that the method further comprises a pressure injection step for pressure injecting the carbon dioxide that is separated in the regeneration step into a pressure injection well in order to increase a fluidity of the fossil fuel buried underground when extracting fossil fuel buried underground, wherein at least a part of product gas produced as the fossil fuel or associated gas thereof that is extracted from a production well for extracting the fossil fuel is reformed in the hydrogen generation step.

According to this arrangement, when extracting fossil fuel by injecting carbon dioxide into the ground, the hydrogen atoms that form part of the hydrocarbons contained in the product gas (including the associated gas) can be effectively utilized.

Effect of the Invention

According to the present invention, in a hydrogen supply system and a hydrogen supply method, the emission of carbon dioxide gas can be reduced, and the energy use efficiency can be improved.

MODE FOR CARRYING OUT THE INVENTION

Preferred embodiments of the present invention are described in the following with reference to the appended drawings.

First Embodiment

Figure 1:
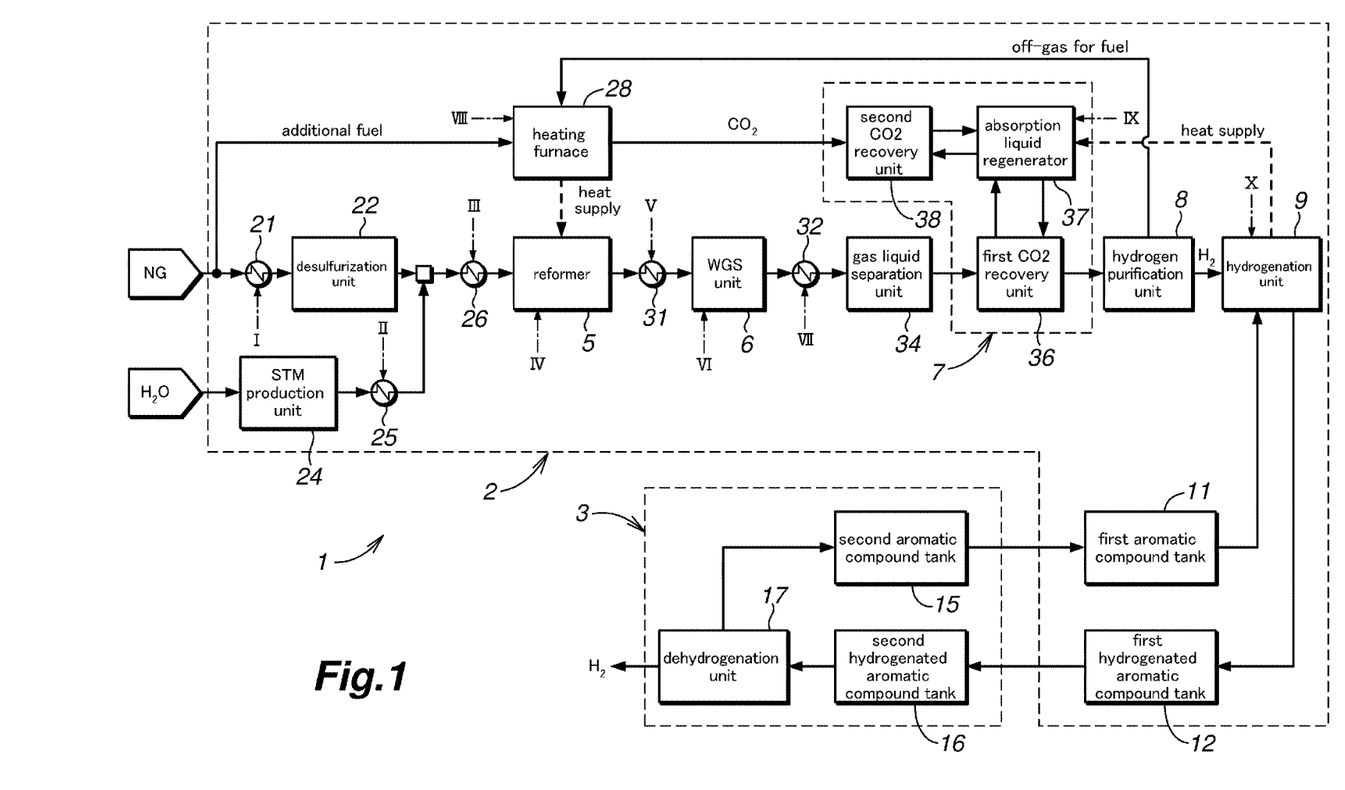
FIG. 1 is a block diagram of a hydrogen supply system given as a first embodiment of the present invention.

FIG. 1 is a block diagram of a hydrogen supply system given as a first embodiment of the present invention. The hydrogen supply system 1 comprises a hydrogenated aromatic compound generation unit 2 for producing hydrogen from a hydrocarbon gas and converting the produced hydrogen into a hydrogenated aromatic compound, and a hydrogen supply unit 3 for producing hydrogen from the hydrogenated aromatic compound. The hydrogenated aromatic compound generation unit 2 and the hydrogen supply unit 3 are typically constructed as plants or devices, and may be located remotely from each other. For instance, the hydrogen supply unit 3 is located in a city or an area adjacent thereto or to a user of hydrogen while the hydrogenated aromatic compound generation unit 2 is preferably located in an area where geological formations suitable for storing carbon dioxide gas are present or in an area adjacent to an extracting site for petroleum or natural gas.

The hydrogenated aromatic compound generation unit 2 of the hydrogen supply system 1 essentially consists of a steam reformer 5, a WGS (water gas shift reaction) unit 6, a carbon dioxide separation unit 7, a hydrogen purification unit (hydrogen separation unit) 8, a hydrogenation unit 9, a first aromatic compound tank 11 and a first hydrogenated aromatic compound tank 12. The hydrogen supply unit 3 comprises a second aromatic compound tank 15, a second hydrogenated aromatic compound tank 16 and a dehydrogenation unit 17. The various components of the hydrogenated aromatic compound generation unit 2 are connected to one another via lines consisting of piping or the like. Likewise, the various components of the hydrogen supply unit 3 are connected to one another via lines consisting of piping or the like.

The hydrocarbon gas that is fed to the hydrogen supply system 1 may consist of natural gas, naphtha, off-gas or the like. The hydrocarbon gas preferably consists of light hydrocarbon gas mainly consisting of methane. In the illustrated embodiment, the hydrocarbon gas consists of natural gas.

First of all, the hydrocarbon gas is supplied to a desulfurization unit 22 via a first heater 21. The hydrocarbon gas may contain sulfur compounds such as mercaptan which may poison the reformer catalyst used in the steam reformer 5. To remove sulfur compounds from the hydrocarbon gas, the desulfurization unit 22 is provided with a Co—Mo catalyst or a Ni—Mo catalyst that allows the sulfur compounds to be removed by hydrodesulfurization and an adsorption agent such as zinc oxide for adsorbing and removing the obtained hydrogen sulfide.

The desulfurized hydrocarbon gas is mixed with steam which is produced by heating and vaporizing water in a STM (steam) production unit 24, and the steam is heated by a second heater 25 before being mixed with the desulfurized hydrocarbon gas. The mixture of the hydrocarbon gas and the steam is heated by a third heater 26, and is then supplied to the steam reformer 5.

The steam reformer 5 is constructed as a tubular reactor consisting of a plurality of pipes. The steam reformer 5 is internally filled with a reformer catalyst, and the hydrocarbon gas and the steam are passed through the interior of the steam reformer 5. The steam reformer 5 is placed in a heat exchanging relationship with a heating furnace 28, and receives heat from the heating furnace 28. The heating furnace 28 is connected to the hydrogen purification unit 8, and receives a supply of fuel (off-gas) containing methane and other components from the hydrogen purification unit 8. A part of the natural gas that is fed to the desulfurization unit 22 may be diverted to the heating furnace 28 as an additional part of the fuel. Fuel is burnt in the heating furnace 28, and the steam reformer 5 is heated by the combustion heat of the heating furnace 28. In a typical arrangement of the steam reformer 5 and the heating furnace 28, the steam reformer 5 is positioned inside the heating furnace 28 so that the steam reformer 5 is heated by the radiation heat obtained by the combustion of fuel in the heating furnace 28.

The reformer catalyst filled in the steam reformer 5 may consist of a nickel catalyst. The steam reformer 5 is heated to a temperature of 800° C. within a shell, and the hydrocarbon gas and the steam are subjected to a steam reforming reaction in the presence of the reformer catalyst according to the chemical equations (1) and (2) given below.

$$C_nH_m + nH_2O \rightleftharpoons nCO + \left(n + \frac{m}{2}\right)H_2 \tag{1}$$

$$C_nH_m + 2nH_2O \rightleftharpoons nCO_2 + \left(2n + \frac{m}{2}\right)H_2 \tag{2}$$

According to the chemical equations (1) and (2), the hydrocarbon gas and the steam are converted into hydrogen, carbon dioxide and carbon monoxide. The steam reforming reaction is an endothermic reaction, and requires a supply of external heat.

The product gas expelled from the steam reformer 5 is supplied to the WGS unit (shift reaction unit) 6 via a first cooler 31. The product gas exchanges heat with a cooling medium such as water of the first cooler 31, and is cooled to a temperature suitable for the shift reaction in the WGS unit 6 while the heat is recovered by the cooling medium. The product gas is cooled to a temperature 250 to 500° C., for instance, in the first cooler 31.

In the WGS unit 6, a water gas shift reaction according to a chemical equation (3) given in the following takes place in the presence of a catalyst such as an iron-chromium catalyst, a copper-chromium catalyst and a copper-zinc catalyst. The temperature of the WGS unit 6 may be selected at an appropriate level by taking into consideration the reaction speed of the shift reaction and the composition of the product. The carbon monoxide and water in the gas are converted into hydrogen and carbon dioxide by the shift reaction. As a result, a large part of the gas that has passed through the WGS unit 6 is converted into hydrogen, carbon dioxide and water.

$$CO + H_2O \rightleftharpoons CO_2 + H_2 \tag{3}$$

The product gas that has passed through the WGS unit 6 is forwarded to a second cooler 32 to be cooled below 100° C. by exchanging heat (heat is recovered) with a cooling medium in the second cooler 32, causing the steam in the product gas to condense. The product gas containing the condensed water is forwarded to a gas liquid separation unit 34 to separate the condensed water therefrom. The gas liquid separation unit 34 may consist of a per se known knockout drum. The product gas from which water is separated in the gas liquid separation unit 34 is then supplied to the carbon dioxide separation unit 7.

The carbon dioxide separation unit 7 is a device that utilizes a carbon dioxide separation and recovery technique based on chemical absorption. The carbon dioxide separation unit 7 of the illustrated embodiment is an apparatus based on chemical absorption using an aqueous alkanolamine solution as the absorption liquid (the absorbent) which selectively dissolves the carbon dioxide. The carbon dioxide separation unit 7 includes a first $CO_2$ recovery unit 36, an absorption liquid regenerator 37 and a second $CO_2$ recovery unit 38. The first $CO_2$ recovery unit 36 and the absorption liquid regenerator 37 are connected to each other so that the absorption liquid may circulate between them. Likewise, the second $CO_2$ recovery unit 38 and the absorption liquid regenerator 37 are connected to each other so that the absorption liquid may circulate between them. The alkanolamine used as the absorption liquid may be in such forms as monoethanolamine, diethanolamine, triethanolamine, methyldiethanolamine, diisopropanolamine, diglycolamine and 2-amino-2-methyl-1-propanol. In this embodiment, the absorption liquid consists of monoethanolamine.

The product gas supplied by the gas liquid separation unit 34 is forwarded to the first $CO_2$ recovery unit 36. The product gas is introduced into a lower part of the first $CO_2$ recovery unit 36 which may consist of a column reactor, and after passing through the interior of the first $CO_2$ recovery unit 36, is expelled from an upper part of the first $CO_2$ recovery unit 36. The absorption liquid flows downward from an upper part to a lower part of the first $CO_2$ recovery unit 36. The product gas supplied to the first $CO_2$ recovery unit 36 thus contacts the absorption liquid so that the carbon dioxide gas is absorbed and removed by the absorption liquid. The product gas freed from carbon dioxide gas is forwarded to the hydrogen purification unit 8.

The absorption liquid that has absorbed the carbon dioxide gas in the first $CO_2$ recovery unit 36 is supplied from a lower part of the first $CO_2$ recovery unit 36 to an upper part of the absorption liquid regenerator 37 which may consist of a column reactor, and is regenerated therein. The absorption liquid regenerator 37 is provided with a heater consisting of a heat exchanger. The absorption liquid supplied to the absorption liquid regenerator 37 is heated by this heater. As will be discussed hereinafter, the heater derives the heat for heating the absorption liquid from the hydrogenation unit 9. In the illustrated embodiment, the heater receives the supply of heat in the form of steam.

The absorption liquid that is heated in the absorption liquid regenerator 37 releases the carbon dioxide that has been absorbed therein. The carbon dioxide that has been separated from the absorption liquid is retrieved from an upper part of the absorption liquid regenerator 37, and the absorption liquid that has been freed from the carbon dioxide is returned from the absorption liquid regenerator 37 to the first $CO_2$ recovery unit 36. The carbon dioxide that has been recovered in the absorption liquid regenerator 37 is stored, and is thereby prevented from being released to the atmosphere. The carbon dioxide can be stored in tanks, or injected or fixed in underground or under the sea. The carbon dioxide may also be used as a material for a methanation reaction.

The hydrogen purification unit 8 separates hydrogen from the product gas which has been freed from carbon dioxide. The hydrogen purification unit 8 may consist of a per se known device such as those based on pressure swing adsorption (PSA) and the use of hydrogen separation membrane, and separates hydrogen from the product gas containing methane and other components. The gas (off-gas) that has been freed from the hydrogen in the hydrogen purification unit 8 contains unreacted components such as methane and carbon monoxide. The hydrogen separated in the hydrogen purification unit 8 is supplied to the hydrogenation unit 9. Meanwhile, the remaining off-gas freed from the hydrogen is supplied to the heating furnace 28, and is burnt therein, thereby heating the steam reformer 5.

The exhaust gas (combustion gas) produced by the combustion in the heating furnace 28 and containing carbon dioxide gas is supplied to the second $CO_2$ recovery unit 38 which is similar in structure to the first $CO_2$ recovery unit 36. The carbon dioxide in the exhaust gas is absorbed in the absorption liquid in the second $CO_2$ recovery unit 38. The absorption liquid that has absorbed the carbon dioxide in the second $CO_2$ recovery unit 38 is supplied to the absorption liquid regenerator 37 to be heated as a regeneration process and releases the carbon dioxide gas that has been absorbed therein in a similar fashion as the absorption liquid that is forwarded from the first $CO_2$ recovery unit 36 to the absorption liquid regenerator 37. The absorption liquid freed from the carbon dioxide is returned to the second $CO_2$ recovery unit 38 via the absorption liquid regenerator 37.

The hydrogenation unit 9 produces a hydrogenated aromatic compound by a hydrogenation reaction of the hydrogen and an aromatic compound in the presence of a hydrogenation catalyst. In the case where the aromatic compound consists of toluene and the hydrogenated aromatic compound consists of methyl cyclohexane, the hydrogenation reaction can be represented by the chemical equation (4) given in the following.

The aromatic compound may include, but is not limited to, monocyclic aromatic compounds such as benzene, toluene and xylene, bicyclic aromatic compounds such as naphthalene, tetralin and methylnaphthalene, and tricyclic aromatic compounds such as anthracene, and these compounds may be used individually or as a mixture of two or more of such components. The hydrogenated aromatic compound is obtained by the hydrogenation of any of such aromatic compounds, and may include, but is not limited to, monocyclic hydrogenated aromatic compounds such as cyclohexane, methyl cyclohexane and dimethyl cyclohexane, bicyclic hydrogenated aromatic compounds such as tetralin, decalin and methyl decalin, and tricyclic hydrogenated aromatic compounds such as tetradecahydroanthracene, and these compounds may be used individually or as a mixture of two or more of such components. The hydrogenated aromatic compound is produced by the hydrogenation of an aromatic compound, and may be selected from any of such hydrogenated aromatic compounds as long as the compound is in a stable liquid form under a normal temperature and pressure condition, and can be converted into a stable aromatic compound when dehydrogenated. Among the various aromatic compounds and hydrogenated aromatic compounds, methyl cyclohexane is preferred as the hydrogenated aromatic compound, and toluene that can be obtained by dehydrogenating methyl cyclohexane is preferred as the aromatic compound.

The hydrogenation catalyst may consist of a per se known catalyst that can be used for hydrogenating an aromatic compound, and, for instance, may include a carrier consisting of alumina or silica and an active metal such as platinum (Pt), palladium (Pd), Nickel (Ni) or the like. The hydrogenation catalyst is filled in the hydrogenation unit 9.

The hydrogenation unit 9 receives a supply of hydrogen from the hydrogen purification unit 8 as well as a supply of an aromatic compound from the first aromatic compound tank 11. In the hydrogenation unit 9, by the hydrogenation reaction represented by the chemical equation (4) in the presence of the hydrogenation catalyst, a hydrogenated aromatic compound is produced from the hydrogen and the aromatic compound. The produced hydrogenated aromatic compound is supplied to the first hydrogenated aromatic compound tank 12 to be stored therein.

The hydrogenation unit 9 includes a heat exchanger which absorbs the heat produced by the hydrogenation reaction, and supplies the absorbed heat to the absorption liquid regenerator 37. The heat exchanger of the hydrogenation unit 9 may consist of a steam drum, for instance, which is positioned in a heat exchanging relationship with the hydrogenation unit 9 and produces steam from water with the heat obtained from the hydrogenation unit 9. The steam produced from the steam drum has a temperature ranging between 100° C. and 200° C. and a pressure ranging between 0.10 MPaA and 1.55 MPaA. The steam drum is connected to the absorption liquid regenerator 37 such that the steam produced in the steam drum may be circulated to the absorption liquid regenerator 37. In other words, the heat generated by the hydrogenation reaction in the hydrogenation unit 9 is transmitted to the absorption liquid regenerator 37 via the heat exchanger which may consist of a steam drum or the like.

The hydrogenated aromatic compound stored in the first hydrogenated aromatic compound tank 12 in liquid form is transported to the second hydrogenated aromatic compound tank 16 of the hydrogen supply unit 3 via a ship, a train or a pipeline. The hydrogenated aromatic compound supplied to the second hydrogenated aromatic compound tank 16 is then supplied to the dehydrogenation unit 17 in which hydrogen and an aromatic compound are produced from the hydrogenated aromatic compound by a dehydrogenation reaction in the presence of a dehydrogenation catalyst. The dehydrogenation reaction is a reaction which is directed from the right to the left in the chemical equation (4). The hydrogen in gas form and the aromatic compound in liquid form produced in the dehydrogenation unit 17 are separated in a gas liquid separator not shown in the drawings, and the hydrogen is supplied to an outside end as hydrogen gas while the aromatic compound in liquid form is stored in a second aromatic compound tank 15. By causing this dehydrogenation reaction in an appropriate manner, an amount of the hydrogen that suits the demand can be produced from the hydrogenated aromatic compound. The aromatic compound stored in the second aromatic compound tank 15 is transported to the first aromatic compound tank 11 of the hydrogenated aromatic compound generation unit 2 via a ship, a train or a pipeline. As discussed above, a recirculation cycle of a hydrogenated aromatic compound and an aromatic compound or a hydrogen supply chain is formed between the hydrogenated aromatic compound generation unit 2 and the hydrogen supply unit 3.

The material balance of the process shown in the block diagram of FIG. 1 for producing hydrogen gas from a hydrocarbon gas or natural gas is shown in Table 1. In Table 1, the total mol number of all the components contained in the natural gas is given as 100 kmol/hr. From Table 1, it can be appreciated that 303.9 kmol/hr of hydrogen gas can be produced from 100 kmol/hr of natural gas.

TABLE 1

Material Balance of Hydrogenated Aromatic Compound Generation Unit

| composition (kmol/hr) | supplied natural gas | supplied steam | reformer inlet | reformer outlet | shift reaction unit outlet | gas liquid seperator outlet | CO2 seperation unit outlet | hydrogen purification unit H2 | hydrogen purification unit off-gas |
|---|---|---|---|---|---|---|---|---|---|
| $CH_4$ | 89.00 | 0.00 | 89.00 | 16.65 | 16.65 | 16.65 | 16.65 | 0.00 | 16.65 |
| $C_2H_6$ | 6.20 | 0.00 | 6.20 | 0.00 | 0.00 | 0.00 | 0.00 | 0.00 | 0.00 |
| $C_3H_8$ | 2.60 | 0.00 | 2.60 | 0.00 | 0.00 | 0.00 | 0.00 | 0.00 | 0.00 |
| $n\text{-}C_4H_{10}$ | 0.70 | 0.00 | 0.70 | 0.00 | 0.00 | 0.00 | 0.00 | 0.00 | 0.00 |
| $i\text{-}C_4H_{10}$ | 1.00 | 0.00 | 1.00 | 0.00 | 0.00 | 0.00 | 0.00 | 0.00 | 0.00 |
| $H_2O$ | 0.00 | 348.00 | 348.00 | 208.69 | 150.35 | 0.00 | 0.00 | 0.00 | 0.00 |

TABLE 1-continued

Material Balance of Hydrogenated Aromatic Compound Generation Unit

| composition (kmol/hr) | supplied natural gas | supplied steam | reformer inlet | reformer outlet | shift reaction unit outlet | gas liquid seperator outlet | CO2 seperation unit outlet | hydrogen purification unit H2 | hydrogen purification unit off-gas |
|---|---|---|---|---|---|---|---|---|---|
| $CO_2$ | 0.00 | 0.00 | 0.00 | 39.95 | 98.30 | 98.30 | 0.00 | 0.00 | 0.00 |
| $H_2$ | 0.00 | 0.00 | 0.00 | 321.52 | 379.86 | 379.86 | 379.86 | 303.89 | 75.97 |
| CO | 0.00 | 0.00 | 0.00 | 59.40 | 1.05 | 1.05 | 1.05 | 0.00 | 1.05 |
| $O_2$ | 0.00 | 0.00 | 0.00 | 0.00 | 0.00 | 0.00 | 0.00 | 0.00 | 0.00 |
| Ar | 0.00 | 0.00 | 0.00 | 0.00 | 0.00 | 0.00 | 0.00 | 0.00 | 0.00 |
| $N_2$ | 0.50 | 0.00 | 0.50 | 0.50 | 0.50 | 0.50 | 0.50 | 0.00 | 0.50 |
| Total | 100.0 | 348.0 | 448.0 | 646.7 | 646.7 | 496.4 | 398.1 | 303.9 | 94.2 |

The heat balance based on the material balance of Table 1 is shown in Table 2. The heat values given in Table 2 represents an influx of heat from outside when positive in sign and an efflux of heat when negative in sign. In the example shown in Table 2, the hydrogenated aromatic compound that is produced by hydrogenating toluene consists of cyclomethlyhexane.

produced. When the entire amount or 303.9 kmol/hr of the hydrogen gas is used for the hydrogenation of toluene, 101.3 kmol/hr of toluene takes part in the hydrogenation reaction according to the chemical equation (4). Because −205 kJ of heat is produced for each mol of toluene in the hydrogenation reaction, −20.80 GJ/hr of heat is produced.

TABLE 2

Heat Balance of Hydrogenated Aromatic Compound Generation Unit

| step | I natural gas preheating | II steam evaporation/ preheating (100-300° C.) | III natural gas/steam preheating | IV reforming (endothermic) | V first cooler heat recovery | VI shift reaction (exothermic) |
|---|---|---|---|---|---|---|
| heat [GJ/hr] | 1.32 | 16.59 | 3.83 | 26.42 | −13.49 | −2.34 |

| step | VII second cooler heat recovery (−100° C.) | VIII heat supply for reforming (combustion of off-gas) | IX heat for absorption liquid regeneration | X hydrogenation reaction (exothermic) | total |
|---|---|---|---|---|---|
| heat [GJ/hr] | −2.11 | −40.64 | 15.25 | −20.80 | −15.97 |

As shown in FIG. 1, a preheating process (I) for the natural gas is performed in the first heater 21, and a preheating process (II) for the steam is performed in the second heater 25. A preheating process (III) for both the natural gas and the steam is performed in the third heater 26. The endothermic process (IV) of the reformer process takes place in the steam reformer 5. A heat recovery process (V) in the first cooler 31 is performed by exchanging heat with the product gas from the steam reformer 5. The exothermic process (VI) of the shift reaction takes place in the WGS unit 6. A heat recovery process (VII) in the second cooler 32 is performed by exchanging heat with the product gas from the WGS unit 6. A heat supplying process (VIII) for the reforming reaction is performed by the combustion of the off-gas that is supplied to the heating furnace 28 from the hydrogen purification unit 8. In the heat supplying process (IX) in the absorption liquid regenerator 37, the supplied heat is used for separating the carbon dioxide from the monoethanolamine that has absorbed the carbon dioxide in the absorption liquid regenerator 37. The exothermic process (X) of the hydrogenation reaction takes place in the hydrogenation unit 9.

As discussed above, when the flow rate of the natural gas is 100 kmol/hr, 303.9 kmol/hr of hydrogen gas can be As shown in Table 2, the total sum of the heat balance in the hydrogenated aromatic compound generation unit 2 of the hydrogen supply system 1 is −15.97 GJ/hr. In other words, the hydrogenated aromatic compound generation unit 2 is able to produce the hydrogenated aromatic compound without requiring a supply of external energy (heat), and allows the produced carbon dioxide gas to be recovered and stored. Suppose that the hydrogen gas is stored in gas form without being converted into a hydrogenated aromatic compound. Then, because the heat generated by the hydrogenation reaction (X: −20.80 GJ/hr) cannot be utilized, it is necessary to supply 4.83 GJ/hr (=−15.97−(−20.80)) of heat from outside.

As discussed above, the hydrogenated aromatic compound generation unit 2 of the hydrogen supply system 1 allows the heat generated by the hydrogenation reaction to be used for the regeneration process of the absorption liquid that has absorbed the carbon dioxide for storing the produced hydrogen in the form of the hydrogenated aromatic compound. Therefore, without requiring the supply of external energy (heat), the hydrogen supply system 1 can recover and store (CSS) the carbon dioxide gas so that the emission of carbon dioxide can be minimized. In the hydrogen supply system 1, because the hydrogen is converted into the hydrogenated aromatic compound before being stored, the subsequent transportation of the hydrogen can be facilitated. Because the hydrogen is converted into the hydrogenated aromatic compound which is suitable for transportation, the hydrogenated aromatic compound generation unit 2 and the hydrogen supply unit 3 can be located geographically remote from each other. Therefore, the hydrogenated aromatic compound generation unit 2 can be located in an area where geological formations suitable for storing carbon dioxide can be found or where hydrocarbons can be extracted so that the cost and energy required for transporting the carbon dioxide and the hydrocarbon gas can be minimized.

Because the carbon dioxide gas that is produced by the combustion of the off-gas in the heating furnace 28 is recovered by the second $CO_2$ recovery unit 38, the amount of carbon dioxide gas that is emitted from the hydrogen supply system 1 can be minimized.

Second Embodiment

Figure 2:
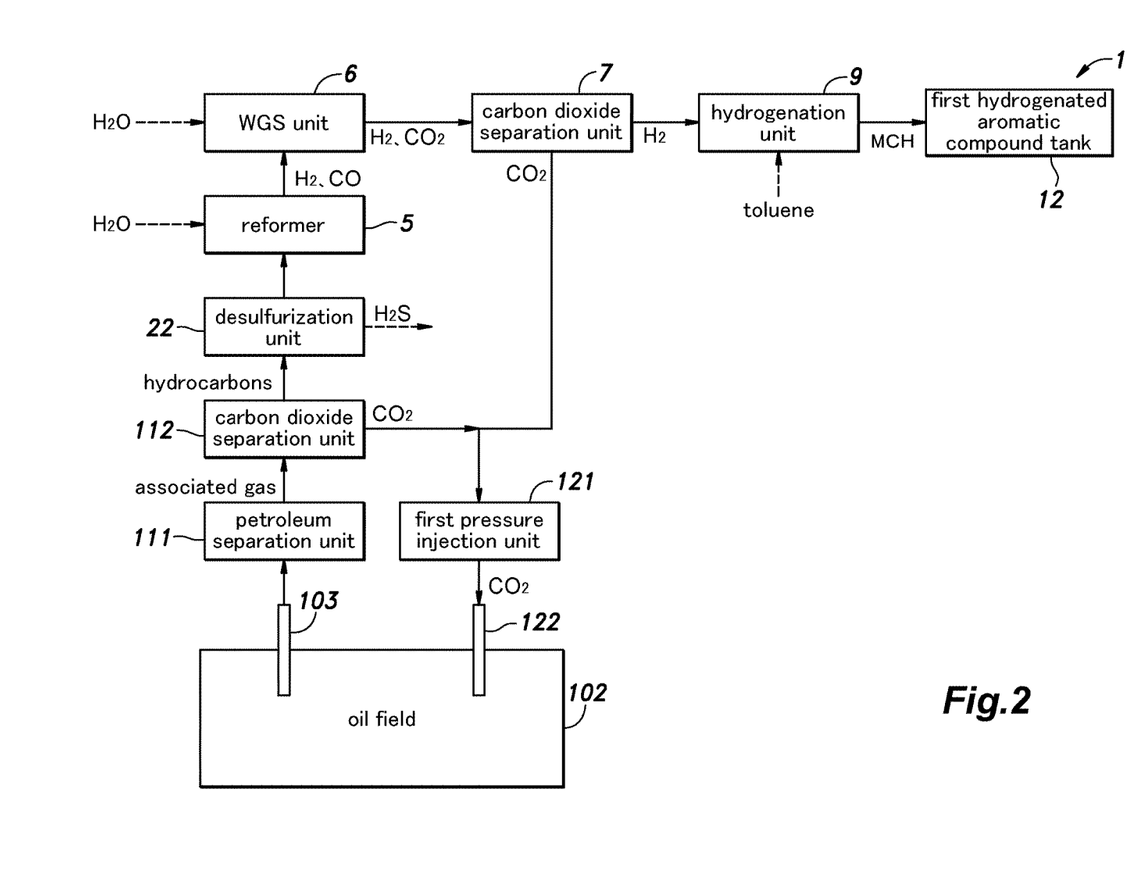
FIG. 2 is a block diagram of a hydrogen supply system given as a second embodiment of the present invention.

FIG. 2 is a block diagram of a hydrogen supply system given as a second embodiment of the present invention. In FIG. 2, the parts corresponding to those of the first embodiment are denoted with like numerals. In FIG. 2, various components of the first embodiment which may also be present in the second embodiment are omitted from the illustration, but it should be noted that such components may be present also in the second embodiment although they are not discussed in the description of the second embodiment. The second embodiment is similar to the first embodiment except for the parts discussed in the following.

Conventionally, as a technique for increasing the recovery efficiency of petroleum that is extracted from an oil field, enhanced oil recovery (EOR) process is known. As different forms of EOR process, various techniques have been developed, such as thermal recovery that reduces the viscosity of the petroleum in order to increase the fluidity thereof by injecting steam into the ground, gas injection that pushes the petroleum from underground by pressure injecting gas into the ground, and chemical injection that promotes the movement of the petroleum by lowering the surface tension thereof with the use of a water solution mainly consisting of a surface reactant. In particular, carbon dioxide injection using carbon dioxide gas ($CO_2$) as the gas to be injected into the ground is gaining favor for the beneficial contribution in reducing global warming.

In a known carbon dioxide injection process, carbon dioxide gas is injected into an oil field to extract petroleum as a mixture with the carbon dioxide, and the liquid (oil) content and the gas content are separated from each other. The separated carbon dioxide is freed from other gas components (associated gas) by using asymmetric polyimide membrane, and the separated carbon dioxide is injected into the oil field once again. See JPH08-158774A, for instance.

In the process of extracting petroleum from an oil field, associated gas or hydrocarbon gas containing ethane, methane, propane and butane is obtained at the same time. In the prior art disclosed in the above mentioned prior art, the carbon dioxide gas contained in the gas freed from the petroleum or oil contents is re-circulated, and utilized, but no consideration was made as to the effective utilization of the hydrocarbon components contained in the associated gas. Conventionally, it was a common practice to dispose such hydrocarbon components by combustion in gas flaring. However, in practicing a carbon dioxide injection process, it is preferable to effectively utilize not only the carbon dioxide but also the associated gas (hydrocarbon components) in view of the effective utilization of available energy and the protection of the environment. Furthermore, the prior art mentioned above is a technology developed for the extraction of petroleum, but it is desirable to effectively utilize the carbon dioxide gas in the product gas of other forms of fossil fuel also in order to reduce the emission of $CO_2$.

In view of such a state of the art, the inventors of this application have discovered the possibility of combining organic chemical hydride process with EOR so that the hydrogen forming a part of the hydrocarbons in the associated gas may be effectively utilized. The hydrogen supply system 1 of the second embodiment and the associated method involve the extraction of fossil fuel such as petroleum and natural gas by injecting fluid (such as carbon dioxide) into the ground, and have a primary object to effectively utilize the hydrogen in the hydrocarbons in the produced gas (including the associated gas). Thus, the hydrogen supply system 1 of the second embodiment functions as a fossil fuel extraction system for extracting (bringing above ground) petroleum (fossil fuel) buried underground in an oil field 102 by injecting carbon dioxide into the ground.

As shown in FIG. 2, an oil well (production well) 103 for extracting petroleum (fossil fuel) is created in the oil field 102, for instance, by drilling Only one oil well 103 is shown here, but, in practice, a plurality of oil wells are drilled because petroleum is typically distributed in underground over a wide area.

In this hydrogen supply system 1, the product fluid that is drawn from the oil well 103 is forwarded to a petroleum separation unit 111 to separate petroleum (crude oil) therefrom. The associated gas that remains from the product fluid after the petroleum has been separated is forwarded to a carbon dioxide separation unit 112 to separate carbon dioxide therefrom. The gas remaining after the carbon dioxide has been separated is forwarded to a desulfurization unit 22 to remove sulfur contents therefrom.

Thus, in the hydrogen supply system 1 of the second embodiment, the hydrocarbon gas that is supplied to the desulfurization unit 22 consists of the associated gas that remains from the product fluid after the petroleum has been recovered therefrom. Similarly as in the first embodiment, the hydrocarbon contents (methane, ethane, propane, butane, etc.) of the desulfurized gas are forwarded to a steam reformer 5 to reform the hydrocarbon contents into a reformed gas (reforming step). The reformed gas is forwarded to a WGS unit 6 to have the carbon monoxide to be shifted to carbon dioxide (shift reaction step). The gas processed by the WGS unit 6 is cooled so that water may be removed therefrom, and is freed from carbon dioxide in a carbon dioxide separation unit 7 (separation step).

The carbon dioxide gas that has been separated in the carbon dioxide separation unit 7 (refer to the absorption liquid regenerator 37 discussed above) is pressurized in a first pressure injection unit 121 and injected into the oil field 102 once again from a $CO_2$ injection well 122 (pressure injection step). The carbon dioxide gas that has been separated in the carbon dioxide separation unit 112 is also forwarded to the first pressure injection unit 121 to be injected into the oil field 102 along with the carbon dioxide gas that is forwarded from the carbon dioxide separation unit 7. By thus providing both the carbon dioxide separation unit 112 for separating the carbon dioxide gas from the associated gas and the carbon dioxide separation unit 7 for separating the carbon dioxide gas produced by the shift reaction, the amount of the carbon dioxide gas that can be pressure injected into the oil field 102 can be increased. It may also be arranged such that the carbon dioxide gas from the carbon dioxide separation unit 112 may be injected into the oil field 102 via a $CO_2$ injection well different from the $CO_2$ injection well 122 via which the carbon dioxide gas from the carbon dioxide separation unit 7 is injected into the oil field 102.

The carbon dioxide gas that has been injected into the ground by the first pressure injection unit 121 changes into supercritical fluid or liquid upon reaching a prescribed depth (pressure), and is mixed with the petroleum in underground to reduce the viscosity thereof (or increase the fluidity thereof). As a result, the amount of petroleum that can be extracted from the oil well 103 can be increased.

The hydrogen gas that has been separated in the carbon dioxide separation unit 7 is forwarded, via a hydrogen purification unit 8 (not shown in FIG. 2), to the hydrogenation unit 9 to be added to a prescribed organic compound serving as a hydrogen carrier in the hydrogenation reaction (hydrogenation step). The organic compound (organic hydride) which has been added with hydrogen is forwarded to a first hydrogenated aromatic compound tank 12 serving as a storage unit to be temporarily stored therein.

Although not shown in the drawing, per se known transportation lines including piping, valves and pumps are provided between the various units in the hydrogen supply system 1 of the second embodiment to transport substances to be processed from one unit to another.

In the hydrogen supply system 1, the hydrogenation of the organic compound in the hydrogenation unit 9, the storage of the organic hydride in the first hydrogenated aromatic compound tank 12 and the production of hydrogen from the organic hydride are performed by an organic chemical hydride process.

For the details of the organic chemical hydride process, reference may be made to Yoshimi Okada et al., "Development of Dehydrogenation Catalyst for Organic Chemical Hydride Method", Catalyst, 2004, 46 (6), p 510-512, ISSN 05598958, Yoshimi Okada et al., "Dehydrogenation Catalyst Development for Organic Chemical Hydride Method and Hydrogen Energy Chain Vision", Catalyst, 2009, 51(6), p 496-498, ISSN 05598958, Yoshimi Okada et al., "Development of Dehydrogenation Catalyst for Organic Chemical Hydride Method with a View of Establishing Large-Volume, Long-Distance Storage and Transportation Technology for Hydrogen Energy", Chemical Engineering, 2010, 74(9), p 468-470, ISSN 03759253, and Yoshimi Okada et al., "Development of Dehydrogenation Catalyst for Organic Chemical Hydride Method for Storage and Transportation of Hydrogen", (Spring Issue, GSC Symposium 2005), Fine Chemical, 2006, 35(1), p 5-13, ISSN 09136150.

The petroleum separation unit 111 is a per se known separator for separating gas components (or associated gas), water and foreign matters from the product extracted from the oil well 103 other than petroleum. The extracted petroleum is stored in a storage facility (not shown in the drawings), and the associated gas separated from the petroleum is forwarded to the carbon dioxide separation unit 112.

The carbon dioxide separation unit 112 is a per se known separator for separating carbon dioxide from hydrocarbon contents contained in the associated gas (such as methane, ethane, propane and butane) by using a membrane separation process. The separation membrane in this embodiment consists of zeolite membrane that has a highly selective transmissivity for carbon dioxide. Zeolite membrane is prepared by forming aquaphilic zeolite film on a porous carrier such as alumina and silica. The aquaphilic zeolite film is heat treated with a temperature of 100 to 800° C.

The separation membrane that can be used in the carbon dioxide separation unit is not limited to zeolite membrane but may consist of other inorganic membranes such as aluminum oxide (alumina) membrane and zirconium oxide (zirconia) membrane. Depending on the application, the $CO_2$ transmission membrane may also consist of organic membrane (such as high polymer membrane) made of organic materials. Such organic material may include, for instance, cellulose acetate, polysulfone, polyethylene, polypropylene and polyacrylonitrile. As the associated gas may contain sulfuric components (such as hydrogen sulfide), the $CO_2$ transmission membrane is required to be resistant against sulfur and otherwise corrosion resistant.

The separation of carbon dioxide gas in the carbon dioxide separation unit 112 is not necessarily based on the membrane separation method, but may also be based on any other per se known separation technique such as a chemical absorption method (for instance, based on absorbing carbon dioxide gas in an alkaline solution such as amine and potassium carbonate through chemical reaction) similar to that employed in the carbon dioxide separation unit 7 (first carbon dioxide separation unit 36) of the first embodiment, and a physical adsorption method (for instance, based on adsorbing carbon dioxide gas directly with an adsorption agent such as zeolite).

The desulfurization unit 22 is filled with a catalyst that allows the sulfur compounds to be removed by hydrodesulfurization and an adsorption agent such as zinc oxide for adsorbing and removing the obtained hydrogen sulfide. The desulfurization unit 22 may be based on a different method other than the use of solid absorption agent or adsorption agent, but also other per se known methods such as the one involving the absorbing of the hydrogen sulfide in an alkaline water solution such as monoethanolamine and diethanolamine. In such a case, other sulfur contents can also be recovered by causing a reaction with hydrogen in the presence of a catalyst, and thereby converting the sulfur contents into hydrogen sulfide.

The steam reformer 5 performs a steam reforming by causing a reaction between the hydrocarbon contents (such as methane, ethane, propane and butane) and steam in the presence of a catalyst (such as a nickel catalyst) at a high temperature (for instance, 800° C.). In the WGS unit 6, in order to increase the concentration of hydrogen in the reformed gas produced in the steam reformer 5, the carbon monoxide is shifted to carbon dioxide under a prescribed temperature condition in the presence of a catalyst. In this case, the concentration of the carbon monoxide is reduced in two stages of shift reaction including a shift reaction at a relative high temperature (about 350 to 420° C.) and a shift reaction at a relatively low temperature (about 200 to 300° C.).

The steam reforming process may be based on any per se known process such as ICI (Imperial Chemical Industries, Ltd.) process and Haldor Topsoe process. In the steam reformer 5, the process of converting the hydrocarbon components into a gas mainly consisting of hydrogen and carbon monoxide may be based on a partial oxidization reforming process. The partial oxidization reaction is mainly based on the following chemical equation (5).

$$C_nH_m + \frac{n}{2}O_2 \rightleftharpoons nCO + \frac{m}{2}H_2 \qquad (5)$$

where n and m are integers.

The carbon dioxide separation unit 7 may be similar in structure to the carbon dioxide separation unit 112 discussed earlier. Because the gas introduced into the carbon dioxide separation unit 7 is substantially free from sulfur contents owing to the desulfurization process performed in the desulfurization unit 22, the $CO_2$ transmission membrane for the carbon dioxide separation unit 7 may be selected without considering the sulfur resistance thereof.

The carbon dioxide separation unit 7 (first carbon dioxide separation unit 36) may be additionally provided with a porous molecular sieve membrane having a prescribed effective pore diameter so that the hydrogen may be further purified following the separation of the carbon dioxide.

The first pressure injection unit 121 injects carbon dioxide gas into a petroleum formation in the oil field 102 according to a per se known EOR (enhanced oil recovery) technique. The first pressure injection unit 121 is provided with a pressure pump for increasing the pressure of the carbon dioxide originally at a substantially atmospheric pressure to a necessary pressure level, and raises the pressure of the carbon dioxide to the necessary pressure level by taking into account the pressure drops that may be caused in the pipeline (not shown in the drawings) for carbon dioxide injection located on the above ground locations of the $CO_2$ injection well 122. The $CO_2$ injection well 122 extends from above the ground to the vicinity of the geological formation containing petroleum.

Thus, the hydrogen supply system 1 of the second embodiment functions as a system for fossil fuel extraction for extracting fossil fuel buried underground by injecting carbon dioxide under pressure, and comprises a steam reformer 5 for producing a reformed gas containing hydrogen and carbon monoxide by reforming at least a part of the fossil fuel in gas form or associated gas that is extracted from a production well, a WGS unit 6 for producing a shift gas containing carbon dioxide gas and hydrogen by causing a shift reaction of the carbon monoxide, a carbon dioxide separation unit 7 for separating the hydrogen and the carbon dioxide in the shift gas from each other, a pressure injection unit 121 for pressure injecting the carbon dioxide that is separated by the separation unit 7 into a pressure injection well in order to increase a fluidity of the fossil fuel buried underground, and a hydrogenation unit 9 for adding the hydrogen separated by the carbon dioxide separation unit 7 to an organic compound by a hydrogenation reaction.

Thus, according to the hydrogen supply system 1 of the second embodiment, when extracting petroleum by injecting carbon dioxide gas into the ground, not only the carbon dioxide contained in the associated gas is effectively utilized but also the hydrogen atoms forming a part of the hydrocarbons contained in the associated gas can be effectively utilized. In particular, by using inorganic membrane made of inorganic material which is superior in corrosion resistance and separation selectivity in the carbon dioxide separation units 7 and 112, the hydrogen atoms forming a part of the hydrocarbons contained in the produced gas can be recovered without compromising the performance in the separation selectivity of the hydrogen and the carbon dioxide. In this case, the carbon dioxide separation unit 7 may combine a plurality of separation units consisting of a chemical absorption process similar to that of the first embodiment and other per se known separation processes such as a physical adsorption process. If desired, the carbon dioxide separation unit 112 may omitted.

Third Embodiment

Figure 3:
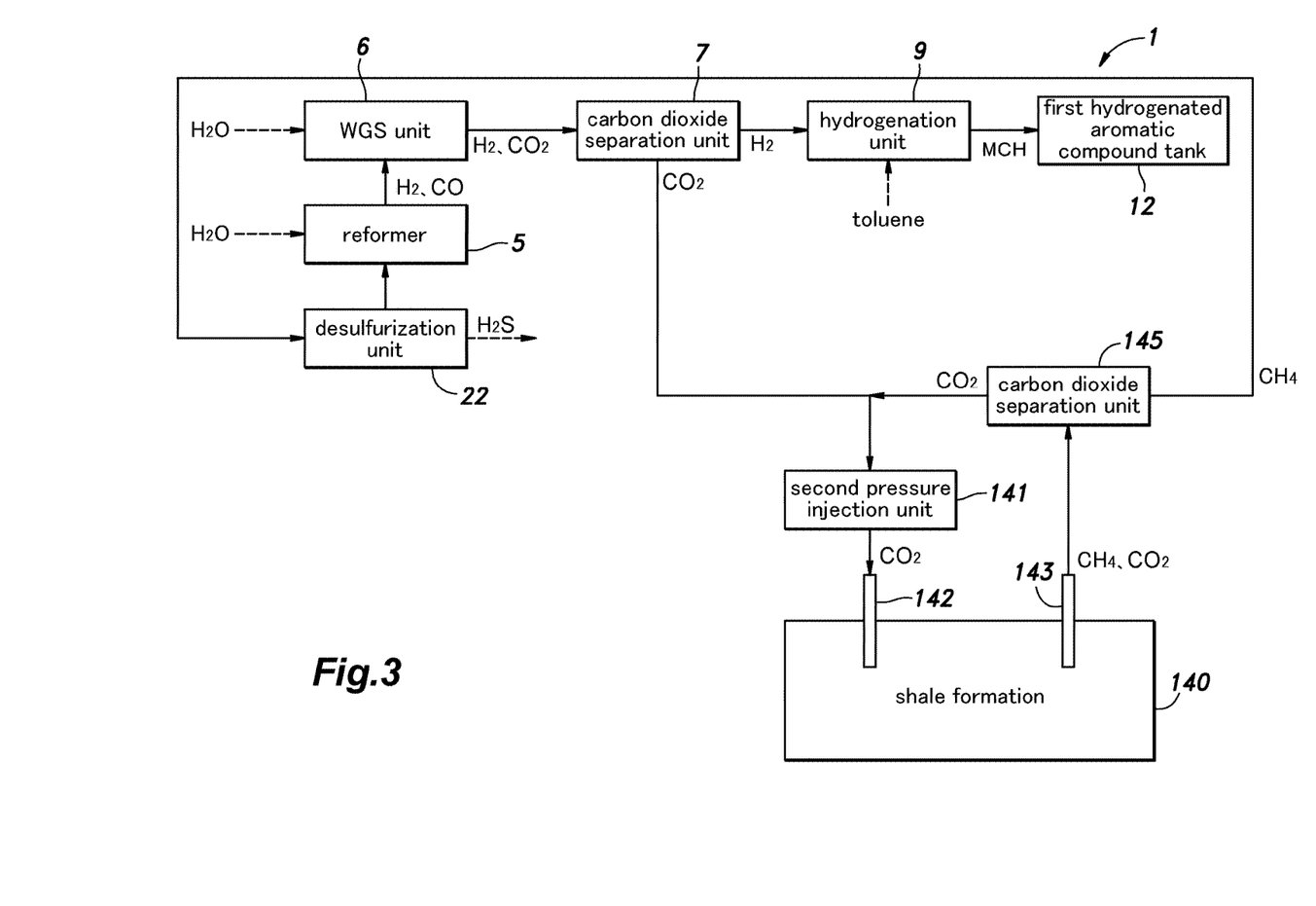
FIG. 3 is a block diagram of a hydrogen supply system given as a third embodiment of the present invention.

FIG. 3 is a block diagram of a hydrogen supply system given as a third embodiment of the present invention. In FIG. 3, the parts corresponding to those of the second embodiment are denoted with like numerals. The third embodiment is similar to the second embodiment except for the parts discussed in the following.

The hydrogen supply system 1 of the third embodiment functions as a fossil fuel extraction system similarly to the second embodiment, but is different from that of the second embodiment in that natural gas (shale gas) is extracted from a shale formation 140 by pressure injecting carbon dioxide. In this hydrogen supply system 1, the second pressure injection unit 141 is similar to the first pressure injection unit 121 of the second embodiment in structure, and is configured to pressure inject carbon dioxide gas into the shale formation 140 via a $CO_2$ injection well 142. The carbon dioxide gas that is injected into the ground turns into a supercritical fluid or liquid upon reaching a prescribed depth (pressure), and fractures the shale rocks in the shale formation by penetrating into the cracks in the shale rocks (or by expanding the fluid paths) in order to increase the fluidity of the natural gas.

As a result, a product gas mainly consisting of methane ($CH_4$) and carbon dioxide gas ($CO_2$) is drawn from the shale formation 140 via a gas well (production well) 143. After having water and foreign matters been removed therefrom, the product gas is forwarded to a carbon dioxide separation unit (second separation unit) 145 to have the carbon dioxide removed therefrom. The carbon dioxide separation unit (second separation unit) 145 is similar in structure to the carbon dioxide separation unit (first separation unit) 7. The remaining gas freed from the carbon dioxide and mainly consisting methane is forwarded to the desulfurization unit 22. Thereafter, the various processes are performed in the desulfurization unit 22, the steam reformer 5, the WGS unit 6, the carbon dioxide separation unit 7, the hydrogenation unit 9 and the first hydrogenated aromatic compound tank 12 in a similar fashion as in the second embodiment.

In the third embodiment, the carbon dioxide gas separated by the carbon dioxide separation unit 7 is pressurized in the second pressure injection unit 141, and pressure injected into the shale formation 140 via the $CO_2$ injection well 142 which extends from the ground surface to an underground area adjacent to a geological formation containing natural gas. The carbon dioxide gas separated by the carbon dioxide separation unit 145 is forwarded to the second pressure injection unit 141, and is pressure injected into the shale formation 140 along with the carbon dioxide gas forwarded from the carbon dioxide separation unit 7. It may also be arranged such that the carbon dioxide gas from the carbon dioxide separation unit 145 may be injected into the shale formation 140 via a $CO_2$ injection well different from the $CO_2$ injection well 142 via which the carbon dioxide gas from the carbon dioxide separation unit 7 is injected into the shale formation 140.

When the concentration of carbon dioxide that is buried with natural gas in a shale formation is low (for instance, below 1%), during the initial stage of operating the hydrogen supply system 1 of the third embodiment, the amount of the carbon dioxide gas that is supplied from the carbon dioxide separation unit 7 and the carbon dioxide separation unit 145 to the second pressure injection unit 141 may not be adequate. In such a case, until the amount of the carbon dioxide gas that is supplied to the second pressure injection unit 141 is stabilized, water and/or air may be injected from the second pressure injection unit 141 to the $CO_2$ injection well 142. The extraction of natural gas by pressure injection of carbon dioxide gas in the hydrogen supply system 1 may be used as an alternative to the extraction of natural gas by a hydraulic fracturing process, but these two processes may also be performed simultaneously. Furthermore, at least a part of the methane that is produced in the carbon dioxide separation unit 145 (to be forwarded to the desulfurization unit 22) may be stored in a storage facility not shown in the drawing for use as fuel, for instance.

Thus, according to the hydrogen supply system 1 of the third embodiment, when extracting natural gas by injecting carbon dioxide gas, not only the carbon dioxide contained in the natural gas is effectively utilized but also the carbon atoms that form a part of the hydrocarbons in the natural gas can be utilized as the carbon dioxide gas to be injected into the ground, and the hydrogen atoms that form a part of the hydrocarbons contained in the natural gas can be effectively utilized as hydrogen energy. In particular, by using inorganic membrane made of inorganic material which is superior in corrosion resistance and separation selectivity in the carbon dioxide separation units 7 and 16, the hydrogen atoms forming the hydrocarbons contained in the produced gas can be recovered without compromising the performance in the separation selectivity of the hydrogen and the carbon dioxide.

Fourth Embodiment

Figure 4:
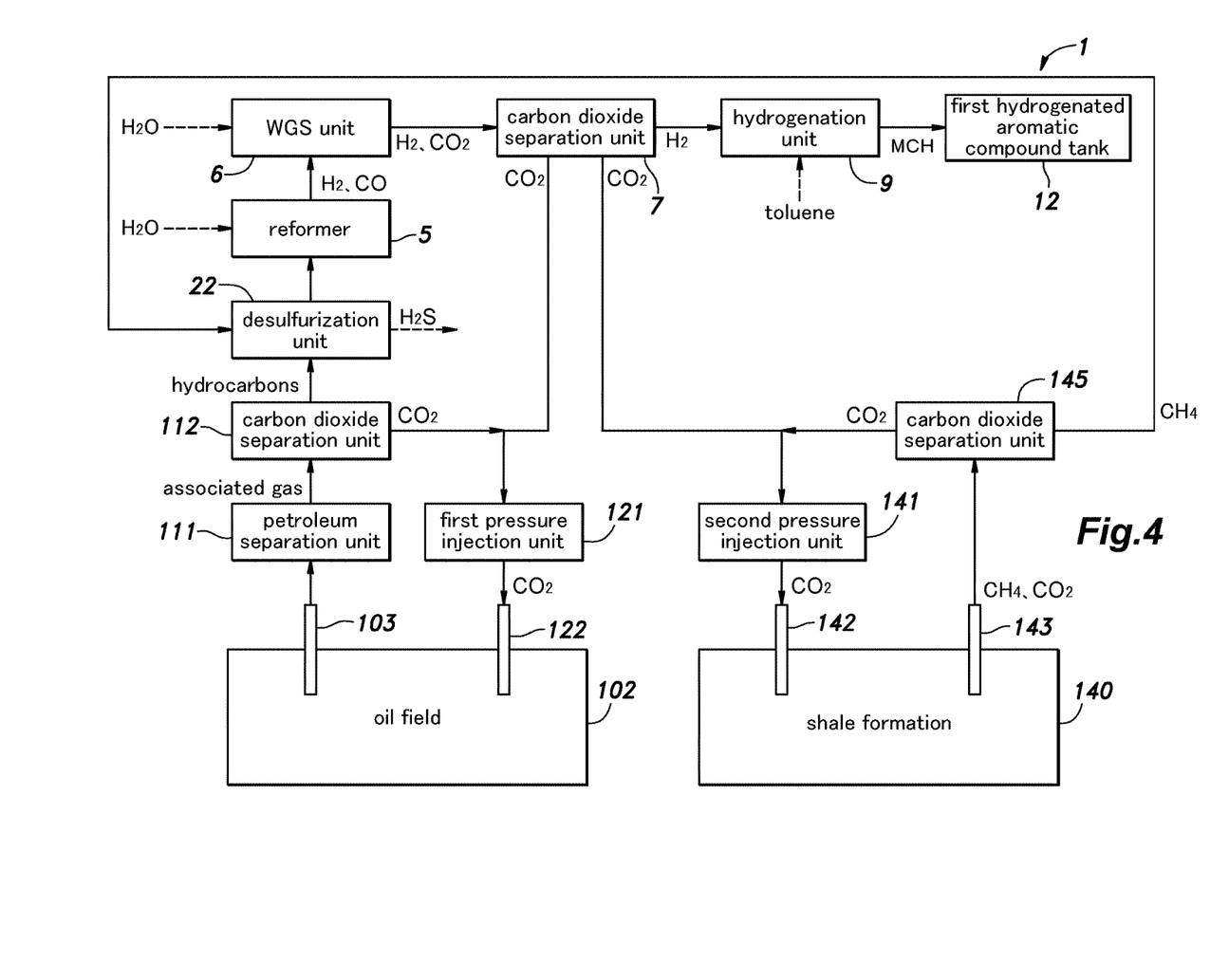
FIG. 4 is a block diagram of a hydrogen supply system given as a fourth embodiment of the present invention.

FIG. 4 is a block diagram of a fossil fuel extraction system given as a fourth embodiment of the present invention. In FIG. 4, the parts corresponding to those of the second embodiment or the third embodiment are denoted with like numerals. The fourth embodiment is similar to the second embodiment or the third embodiment except for the parts discussed in the following.

In the hydrogen supply system 1 of the fourth embodiment, carbon dioxide gas is injected into both an oil field 102 and a shale formation 140 so that both petroleum and natural gas may be extracted. In other words, this hydrogen supply system 1 shares and combines the desulfurization unit 22, the steam reformer 5, the WGS unit 6, the carbon dioxide separation unit 7, the hydrogenation unit 9 and the first hydrogenated aromatic compound tank 12 of the hydrogen supply systems 1 of the second and third embodiments.

In the carbon dioxide separation unit 7 of the fourth embodiment, the separated carbon dioxide is supplied to both the first pressure injection unit 121 and the second pressure injection unit 141. The carbon dioxide separation unit 7 is configured such that the amount of carbon dioxide gas that is supplied to each of the first pressure injection unit 121 and the second pressure injection unit 141 can be determined depending on the need and the operating condition of the first pressure injection unit 121 or the second pressure injection unit 141 as the case may be. In other words, by injecting carbon dioxide gas into both the oil field 102 and the shale formation 140 to extract fossil fuel (petroleum and natural gas) buried in the oil field 102 and the shale formation 140 with the common single hydrogen supply system 1, the amounts of injected carbon dioxide can be adjusted more easily, and the fossil fuel can be extracted in a more stable manner.

Although the present invention has been described in terms of preferred embodiments thereof, it is obvious to a person skilled in the art that various alterations and modifications are possible without departing from the spirit of the present invention. In the foregoing embodiments, the heat generated from the hydrogenation reaction in the hydrogenation unit 9 was converted into steam that is transported to the absorption liquid regenerator 37, but the heat that is to be transported is not necessarily in the form of steam. For instance, the absorption liquid regenerator 37 and the hydrogenation unit 9 may be positioned adjacent to each other so that the heat may be directly exchanged between them. It is also possible to arrange such that a line (piping) conducting the absorption liquid is passed through the hydrogenation unit 9. Alternatively, a line (piping) conducting the reactants and the product of the hydrogenation unit 9 may be passed through the absorption liquid regenerator 37.

The first $CO_2$ recovery unit 36 and the second $CO_2$ recovery unit 38 were provided separately from each other in the foregoing embodiment, but the first $CO_2$ recovery unit 36 and the second $CO_2$ recovery unit 38 may also be formed as a common unit so that the product gas that has passed through the gas liquid separation unit 34 and the exhaust gas from the heating furnace 28 may pass through the common $CO_2$ recovery unit.

The hydrogenated aromatic compound generation unit 2 and the hydrogen supply unit 3 may be positioned geographically either remote from each other or adjacent to each other. When the hydrogenated aromatic compound generation unit 2 and the hydrogen supply unit 3 are located adjacent to each other, the second aromatic compound tank 15 and the second hydrogenated aromatic compound tank 16 may be omitted. The hydrogen supply unit 3 may be constructed as a plant (a large facility), but may also be formed as a compact unit for home installation or for use onboard a vehicle.

Furthermore, in the second to the fourth embodiments of the present invention, not only carbon dioxide alone may be injected into the injection well but also a mixture of carbon dioxide and any other gas may be injected into the injection well. The injection of carbon dioxide gas according to the present invention is not limited to the use in the EOR (enhanced oil recovery) technique in a narrow sense but also in fossil fuel extraction by gas injection in a broad sense. The various elements used in the system and method for fossil fuel extraction of the illustrated embodiment are not entirely essential for the present invention, but may be partly omitted and substituted without departing from the spirit of the present invention.

GLOSSARY OF TERMS

1 hydrogen supply system
2 hydrogenated aromatic compound generation unit
3 hydrogen supply unit
5 steam reformer
6 WGS unit (shift reaction unit)
7 carbon dioxide separation unit
8 hydrogen purification unit
9 hydrogenation unit
11 first aromatic compound tank
12 first hydrogenated aromatic compound tank
15 second aromatic compound tank
16 second hydrogenated aromatic compound tank
17 dehydrogenation unit
21 first heater
22 desulfurization unit
24 STM production unit
25 second heater
26 third heater
28 heating furnace
31 first cooler
32 second cooler
34 gas liquid separation unit
36 first $CO_2$ recovery unit (first absorber)
37 absorption liquid regenerator 38 second CO₂ recovery unit (second absorber)
102 oil field
103 oil well (production well)
111 petroleum separation unit
112 carbon dioxide separation unit
114 reformer
121 first pressure injection unit
140 shale formation
141 second pressure injection unit
142 CO₂ injection well
143 gas well (production well)
145 carbon dioxide separation unit

The invention claimed is:

1. A hydrogen supply system, comprising:
a reformer configured to perform steam reforming of a hydrocarbon mainly consisting of methane to produce a gas containing hydrogen and carbon dioxide;
a shift reaction unit configured to produce the gas containing hydrogen and carbon dioxide by causing a water gas shift reaction of a gas obtained from the reformer;
a first absorber configured to absorb the carbon dioxide contained in the gas obtained from the shift reaction unit in an absorption liquid to thereby produce a gas freed from the carbon dioxide;
a hydrogen purification unit configured to receive the gas produced by the first absorber and separate the hydrogen from the gas received from the first absorber such that the separated hydrogen constitutes purified hydrogen;
a hydrogenation reaction unit connected to the hydrogen purification unit to receive the purified hydrogen from the hydrogen purification unit and configured to produce a hydrogenated aromatic compound by causing a hydrogenation reaction of an aromatic compound with the purified hydrogen received from the hydrogen purification unit;
a regenerator connected to the first absorber and configured to separate the carbon dioxide from the absorption liquid by re-circulating the absorption liquid from the first absorber and heating the absorption liquid with heat generated from the hydrogenation reaction;
a heating furnace configured to receive the gas remaining after the hydrogen is separated by the hydrogen purification unit, combust the received gas, and supply combustion heat generated thereby to the reformer; and
a pressure injection unit configured to pressure inject the carbon dioxide that is separated from the absorption liquid by the regenerator into a pressure injection well in order to increase a fluidity of the fossil fuel buried underground when extracting fossil fuel buried underground, the reformer being connected to a production well and configured to extract the fossil fuel and reform at least a part of product gas produced as the fossil fuel or associated gas thereof that is extracted from the production well.

2. The hydrogen supply system according to claim 1, further comprising
a second absorber configured to absorb carbon dioxide generated from the heating furnace in an absorption liquid;
wherein the second absorber re-circulates the absorption liquid to the regenerator, and the absorption liquid that has absorbed the carbon dioxide in the second absorber is heated in the regenerator to separate the carbon dioxide therefrom.

3. The hydrogen supply system according to claim 1, wherein the heat generated by the hydrogenation reaction is supplied to the regenerator as steam at a temperature of 100 to 200° C. and a pressure of 0.10 to 1.62 MPaA.

4. The hydrogen supply system according to claim 1, further comprising a first separation unit having an inorganic membrane configured to separate the hydrogen and the carbon dioxide in the gas obtained from the shift reaction unit from each other.

5. The hydrogen supply system according to claim 4, wherein the production well is provided in a shale formation for extracting natural gas, and the natural gas is extracted as the fossil fuel.

6. The hydrogen supply system according to claim 5, wherein the product gas includes the natural gas extracted from the shale formation and the pressure injected carbon dioxide, and the system further comprises a second separation unit configured to separate the natural gas and the carbon dioxide of the product gas from each other, the reformer reforming at least part of the natural gas separated by the second separation unit, and the pressure injection unit pressure injecting the carbon dioxide separated by the second separation unit into the pressure injection well in order to increase a fluidity of the fossil fuel buried underground.

7. The hydrogen supply system according to claim 1, wherein the production well is provided in an oil field for extracting petroleum, and the petroleum is extracted as the fossil fuel.

8. The hydrogen supply system according to claim 1, further comprising a desulfurization unit configured to remove a sulfur content from the product gas before the product gas is reformed by the reformer.

* * * * *